United States Patent [19]

Goldberg et al.

[11] Patent Number: 5,194,544
[45] Date of Patent: Mar. 16, 1993

[54] UV ABSORBING VINYL MONOMERS AND POLYMERS AND OCULAR IMPLANTS PREPARED THEREFROM

[75] Inventors: Eugene P. Goldberg, Gainesville, Fla.; Fu-Mian Li, Beijing, China; Ching-Wang Luo, Plantation, Fla.

[73] Assignee: University of Florida, Gainesville, Fla.

[21] Appl. No.: 542,932

[22] Filed: Jun. 25, 1990

Related U.S. Application Data

[60] Division of Ser. No. 239,424, Sep. 1, 1988, Pat. No. 4,985,559, which is a continuation-in-part of Ser. No. 108,690, Oct. 15, 1987, abandoned.

[51] Int. Cl.$^5$ .................. C08F 28/06; C07D 513/00; C07D 279/18; C07D 279/22
[52] U.S. Cl. ..................... 526/257; 523/108; 544/34; 544/38; 544/39
[58] Field of Search .................. 523/108; 544/34, 35, 544/38, 39; 526/257

[56] References Cited

U.S. PATENT DOCUMENTS

4,985,559  1/1991  Goldberg et al. .................. 544/34

Primary Examiner—Paul R. Michl
Assistant Examiner—Peter Szekely
Attorney, Agent, or Firm—Kerkam, Stowell, Kondracki & Clarke

[57] ABSTRACT

An ultraviolet light-absorbing polymer which comprises a homopolymer of a polymerizable monomer having the structure:

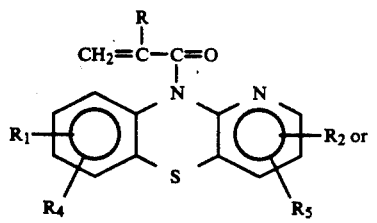

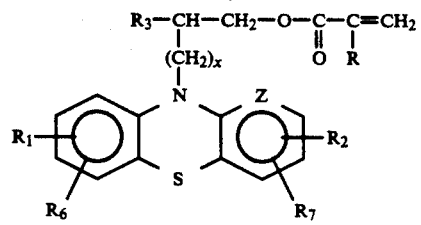

wherein:
Z is N or —CH—,
R is H or $CH_3$,
$R_1$ and $R_2$ may be the same or different and are H, alkyl or alkyloxy having from 1 to 20 carbon atoms, alkylcarboxy having from 2 to 20 carbon atoms, arylcarboxy having from 7 to 25 carbon atoms or hydroxyl;
$R_3$ is H, hydroxyl, hydroxyalkyl having from 1 to 20 carbon atoms or siloxy;
$R_4$, $R_5$, $R_6$ and $R_7$ may be the same or different and are H or halogen;
x is an integer from 1 to 20; or
a copolymer thereof with an ethylenically unsaturated comonomer, the copolymer comprising an ultraviolet light-absorbing effective amount of the ultraviolet light-absorbing polymerizable monomer.

20 Claims, 4 Drawing Sheets

UV ABSORBING VINYL MONOMERS AND POLYMERS AND OCULAR IMPLANTS PREPARED THEREFROM

BACKGROUND OF INVENTION

This is a division of application Ser. No. 07/239,424 filed Sep. 1, 1988 now U.S. Pat. No. 4,985,559, issued Jan. 15, 1991, which was a continuation-in-part of application Ser. No. 07/108,690 filed Oct. 15, 1987 now abandoned.

FIELD OF THE INVENTION

The present invention relates to certain novel UV light absorbing monomers and polymers and lenses prepared therefrom.

PRIOR ART

There exists the need for the provision of polymeric materials which are not degraded by or otherwise affected by ultraviolet light. Polymeric materials such as implants, lenses, etc., presently suffer from the disadvantage of ultraviolet light-induced degradation. Currently employed polymeric materials for the manufacture of ocular lenses, etc., incorporate stabilizers which absorb a large quantity of the ultraviolet light or quench the energy which results from excitation of groups in the polymeric material as a result of ultraviolet radiation. The extractability of these stabilizers, however, detracts from their usefulness since they are subject to extraction by body fluids or other liquids thereby raising the problems of contamination, toxicity, etc.

It is also necessary, in some instances, to provide lenses manufactured from materials which absorb ultraviolet light thereby overcoming a condition in the eye which prevents the ordinary absorption of ultraviolet light. For example, the aphakic eye contains no crystalline lens which ordinarily absorbs light at wavelengths from about 300 up to about 400 nm. Since the entire spectrum of light striking the retina in the aphakic eye is significantly different from that in the normal eye, corrective means are necessary to restrict the spectrum striking the retina therein.

Copolymerizable monomers containing functional groups capable of absorbing ultraviolet light have been synthesized. The copolymerization of such monomers with those ordinarily employed to manufacture lenses and ocular implants, etc., results in the formation of materials resistant to degradation upon exposure to ultraviolet light with decreased extractability and volatility. See, for example, U.S. Pat. Nos. 4,304,895; 4,310,650; 3,162,676; 4,390,676 and 4,528,311.

The monomers and systems described by the above-listed patents use relatively inefficient benzophenone or benzotriazole UV absorbing vinyl monomers and therefore require the inclusion of relatively large amounts of the UV absorbing monomer in the copolymer. For UV absorbing intraocular lenses with optics capable of absorbing 95% of the light below 400 nm (5% transmission), for example, concentrations of 5-10 wt % of benzophenone and 1-5% or more of benzotriazole monomers are required. The use of such high UV absorbing comonomer concentrations is accompanied by significant inefficiency in copolymerization with methylmethacrylate, for example, due to the radical inhibitor properties of the UV absorber; thereby resulting in substantially reduced monomer conversions, low molecular weight polymers, and large amounts of UV absorber unreacted monomers which can act as biotoxic impurities.

Accordingly, it is an object of the present invention to provide novel ultraviolet light absorbing monomers which are more efficient UV absorbers and are capable of copolymerization with monomers in relatively small amounts to prepare ocular materials capable of absorbing ultraviolet light.

The provision of such a monomer enables the preparation of ocular materials having an extremely low concentration of the ultraviolet absorber thereby ensuring optimum long-term implant biocompatibility and usefulness of the lens.

SUMMARY OF THE INVENTION

These and other objects are realized by the present invention which provides certain novel UV light absorbing polymerizable monomers having the structure:

Wherein:

Z is N or —CH—,

R is H or CH$_3$,

R$_1$ and R$_2$ may be the same or different and are H, alkyl or alkyloxy having from 1 to 20 carbon atoms, alkylcarboxy having from 2 to 20 carbon atoms, arylcarboxy having from 7 to 25 carbon atoms or hydroxyl, R$_3$ is H, hydroxyl, hydroxyalkyl having from 1 to 20 carbon atoms or siloxy;

R$_4$, R$_5$, R$_6$ and R$_7$ may be the same or different and are H or halogen; and x is an integer from 1 to 20; or a homopolymer thereof; or a copolymer thereof with an ethylenically unsaturated monomer, the copolymer comprising an ultraviolet light absorbing effective amount of the ultraviolet light absorbing, polymerizable monomer.

The term "aryl" is intended to include any aromatic group, preferably a hydrocarbyl group, optionally substituted with non-toxic, pharmaceutically acceptable substituents which do not affect the UV absorbing characteristics of the monomer or resulting polymer.

BRIEF DESCRIPTION OF THE DRAWINGS

FIGS. 4-6 depict examples of ocular implants according to the present invention.

DETAILED DESCRIPTION OF THE INVENTION

The monomers of the present invention are valuable in that they are potent ultraviolet light absorbers particularly between about 300 nm and about 450 "MN" or more. Copolymerization of the monomers of the present invention with monomers currently employed to prepare optical devices such as contact and intraocular lenses as well as lenses used in spectacles results in the production of lenses capable of absorbing UV light. Since the UV absorbing monomers form a part of the polymer chain there is little likelihood of contamination of the eye by extraction or leaching of the monomeric material into the eye or surrounding tissue. Moreover, the polymers prepared therefrom achieve a high degree of ultraviolet light absorption using extremely small amounts of the monomer, generally less than 1%, by weight, based on the weight of the polymer The novel monomers of the invention may be polymerized or copolymerized with other vinyl-type monomers by conventional methods of vinyl polymerization including free radical and gamma radiation initiation.

Suitable monomers for copolymerization with the monomers of the present invention are those typically used to prepare lens materials, e.g., alkyl acrylates and methacrylates, e.g., methylacrylate, methylmethacrylate, other acrylic vinyl monomers, hydrophilic vinyl monomers suitable for preparation of hydrogels, such as N-vinylpyrrolidone (NVP), hydroxyethylmethacrylate (HEMA), hydroxyethylacrylate (HEA) hydroxypropylacrylates, acrylamide (AA), AA derivatives, and cross-linkable divinyl monomers such as bisacrylamides, bisacrylates, ethylene glycol dimethacrylates, bisallylcarbonates, etc. In general, vinyl and divinyl monomers which polymerize by normal methods of addition polymerization and which have suitable copolymerization reactivity ratios are useful.

The preferred UV absorbing monomers of the present invention include substituted phenothiazine and azaphenothiazine compounds having the structures:

10-acryloyl-azaphenothiazine (AATPT)

I

10-methacryloyl-azaphenothiazine (MAATPT)

II

γ-10-(2-acetylphenothiazinyl)-β-hydroxypropyl methacrylate (MHAPT)

III

γ-10-(azaphenothiazinyl)-β-hydroxypropyl methacrylate (GMAAPT)

IV

10-methacryloylphenothiazine (MAPT)

V

γ-10-(2-chlorophenothiazinyl)-β-hydroxypropyl methacrylate (MHACPT)

VI

γ-10-(2-chloro-8-benzoylphenothiazinyl)-β-hydroxypropyl methacrylate (MHBCPT)

VII

β-10(2-acetylphenothiazinyl)-ethyl methacrylate (EMAPT)

The novel substituted phenothiazine and azaphenothiazine monomers of this invention are synthesized by conventional organic syntheses involving acetylation, alkylation, esterification, etc., from readily available phenothiazine and azaphenotriazine compounds as shown in the examples.

The monomers of this invention may be incorporated by copolymerization into a wide variety of compatible polymers wherein absorption of ultraviolet light is desirable. For example, they may be incorporated into acrylic polymers such as polymethylmethacrylate, polybutylmethacrylate, polyethylacrylate, etc. and acrylic copolymers with other vinyl monomers, into linear or cross-linked vinyl polymers (especially with divinyl bisacrylates, bisacrylamides, and biscarbonates), and with a wide range of hydrogel compositions.

The UV absorbing copolymers of this invention are particularly adapted for constructing ocular articles such as lenses, ocular implants, intraocular lenses, contact lenses, keratoprostheses, as well as plastic parts, films and fibers which benefit from absorption of and resistance to UV light.

A useful, quantitative measurement for ultraviolet absorbing properties, i.e., UV "cut-off", is that wavelength in the ultraviolet-visible spectrum at which the transmission (T) for a 1 mm sample falls to 5%. To obtain a 5% T value at 400 nm, it has previously been usually necessary with the known polymerizable monomers to employ more than 1-2%, by weight of the monomer, based on the weight of the polymer, often as much as 5-10%. The monomers of the present invention yield 5% T values using less than 1 wt % in many polymers and, for polymers such as polymethacrylate with preferred monomers, as little as 0.2-0.3 wt % is required.

The development of ocular materials with 5% T UV cut-offs at 420-440 nm has been compromised by the adverse properties of these compounds which require such high concentrations. The present invention enables the achievement of, e.g., 440 nm cut-offs using as little as 0.5 wt % of the monomer in some compositions.

In addition to ocular materials, the polymers of the invention are also useful in manufacturing films, e.g., wrapping materials, windows, skylights, glazing materials, automobile light housings, etc., to absorb UV light and to enhance the UV stability of polymers.

To achieve optimum ultraviolet light absorption and retain optimum optical qualities, it is preferred that the copolymers contain from about 0.1% to about 5%, by weight, of the UV absorbing monomer.

EXAMPLE 1

This example illustrates the preparation of a copolymer, poly (MMA-MHAPT), of methylmethacrylate (MMA) and [γ-10-(2-acetylphenothiazinyl)-β-hydroxypropyl methacrylate (MHAPT) (Formula III), and the synthesis of MHAPT.

Preparation of γ-10-(2-acetylphenothiazinyl-β-hydroxypropyl methacrylate (MHAPT)

0.20 g (0.0086 mol) of sodium hydride was added carefully to a solution of 2-acetylphenothiazine (2 g, 0.0083 mol) in 150 ml tetrahydrofuran under agitation below 5° C. A solution of glycidyl methacrylate (1.88 g, 0.013 mol) in 10 ml tetrahydrofuran was added dropwise to above solution. The reaction was kept at room temperature for 48 hours. After the solvent was removed, the residue was washed with dilute HCl and water. Dried. 2.3 g of product was obtained by recrystallization with ethyl acetate.

Preparation of MMA-MHAPT UV Absorbing Copolymer

MHAPT dissolved readily in MMA. Copolymer compositions with different concentrations of MHAPT were prepared using AIBN as a radical polymerization initiator and heating the comonomer mixture to 60°-70° C. Transparent copolymer slabs were cast in glass molds (1.0 mm thick) with 0.05%, 0.1%, 0.25%, 0.3%, 0.5%, and 2% polymerizable UV absorber, MHAPT. Transmission spectra of these slabs in the UV and visible range were recorded. The following table lists the compositions and the corresponding wavelength at 5% transmission.

| | MMA (wt %) | MHAPT (wt %) | AIBN (wt %) | λ at 5% Transmission (nm) |
|---|---|---|---|---|
| #1 | 99.95 | 0.05 | 0.5 | 331 |
| #2 | 99.9 | 0.10 | 0.5 | 368 |
| #3 | 99.75 | 0.25 | 0.5 | 403 |
| #4 | 99.7 | 0.30 | 0.5 | 410 |
| #5 | 99.5 | 0.50 | 0.5 | 444 |
| #6 | 98 | 2.0 | 0.5 | 473 |

Figure 2:
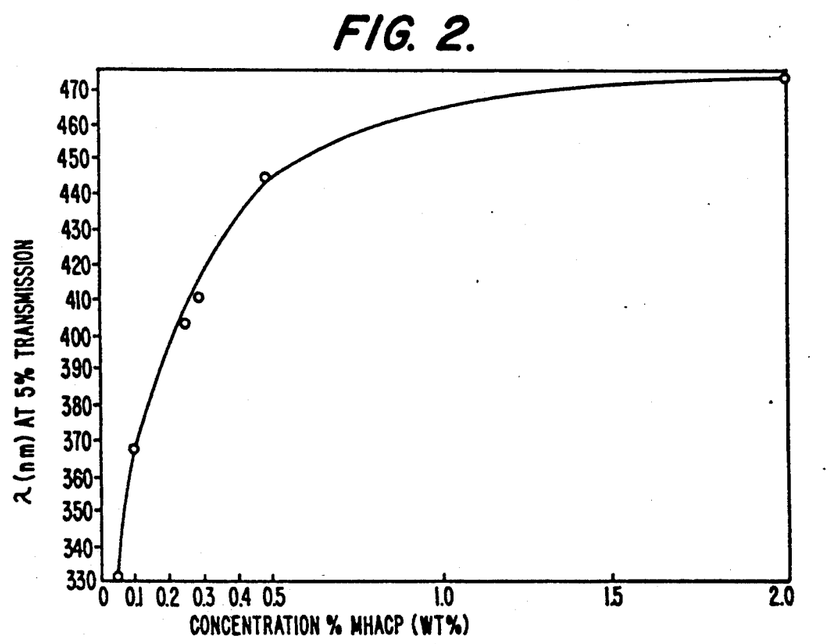

These results were plotted, wt % MHAPT versus λ at 5% transmission, in FIG. 2 and show that with as little as 0.25% UV absorbing comonomer, the 5% T UV cut-off is greater than 400 nm and that with as little as 0.5% UV comonomer, greater than 440 nm 5% T cut-off is achieved for PMMA compositions.

EXAMPLE 2

These examples illustrate the preparation of substituted azaphenothiazine compounds of the invention, 10-acryloyl-azaphenothiazine (AATPT) and 10-methacryloyl-azaphenothiazine (MAATPT).

I. A solution of 2.0 g DCC in 30 ml methylene chloride was added dropwise to a solution of 2.0 g azaphenothiazine and 1.0 g acrylic acid in 70 ml methylene chloride under agitation, 0°-5° C. The reaction was kept at room temperature for 24 hrs. Filtered out the precipitate. The solvent was evaporated. 1.1 g AATPT yellow product was obtained by recrystallization with cyclohexane.

II 2.0 g of azaphenothiazine and 1.5 g of acrylic anhydride was dissolved in 50 ml dioxane. The reaction was kept at 60° C. for 1 hr and then at room temperature overnight. After the evaporation of the solvent, the crude AATPT product was recrystallized with cyclohexane at a yield of 20-30%.

III. The above procedures yield MAATPT using methacrylic acid (Method I) or methacrylic anhydride (Method II).

EXAMPLE 3

This example illustrates the preparation of γ-10-(2-chlorophenothiazinyl)-β-hydroxypropyl methacrylate (MHACPT).

0.30 g of sodium hydride was added carefully to a solution of 2.0 g 2-chlorophenothiazine in 75 ml dioxane under agitation, at 60° C. Then the temperature was raised to 100° C., and was kept for 6 hrs. 3.0 g of glycidyl methacrylate in 10 ml dioxane was added dropwise to above solution and kept for 8 hrs. Evaporated the solvent, the solid was washed thoroughly with dilute HCl and water. The product was recrystallized with 95% ethanol.

EXAMPLE 4 a) The procedure of Example 3 was repeated utilizing 2-acetylphenothiazine to prepare γ-10-(2-acetylphenothiazinyl)-β-hydroxypropyl methacrylate (MHAPT).

b) The procedure of Example 3 was repeated utilizing 2-chloro-8-benzoylphenothiazine to prepare γ-10-(2-chloro-8-benzoylphenothiazinyl)-β-hydroxypropyl methacrylate (MHBCPT).

EXAMPLE 5

β-10-(2-Acetylphenothiazinyl)-ethyl Methacrylate (EMAPT)

i) 10-(β-Hydroxyethyl)-2-acetylphenothiazine. A mixture of 2.0 g of 2-acetylphenothiazine and 1.5 g of ethylene carbonate was heated at 200° C. for 4 hrs. Upon cooling of the above reaction mixture, the solidified mixture was dissolved in ethanol. A brown product was obtained by recrystallization with ethanol-water.

ii) β-10-(2-Acetylphenothiazinyl)ethyl Methacrylate. A 2.0 g of β-N-hydroxyethyl-2-acetylphenothiazine was dissolved in 100 ml of methyl methacrylate, and the transesterification was performed for 24 hrs by using 0.1 g of p-toluenesulfonic acid as catalyst and 0.02 g of hydroquinone as inhibitor. After removal of methyl methacrylate, the residue was washed thoroughly with sodium carbonate solution and water. A light brown product was obtained by recrystallization with ethanol-water.

EXAMPLE 6

This example illustrates the use of the UV absorbing monomers of this invention to form transparent, flexible, hydrogel compositions possessing useful UV absorbing properties with relatively low concentrations of covalently bound UV absorbers.

Figure 3:
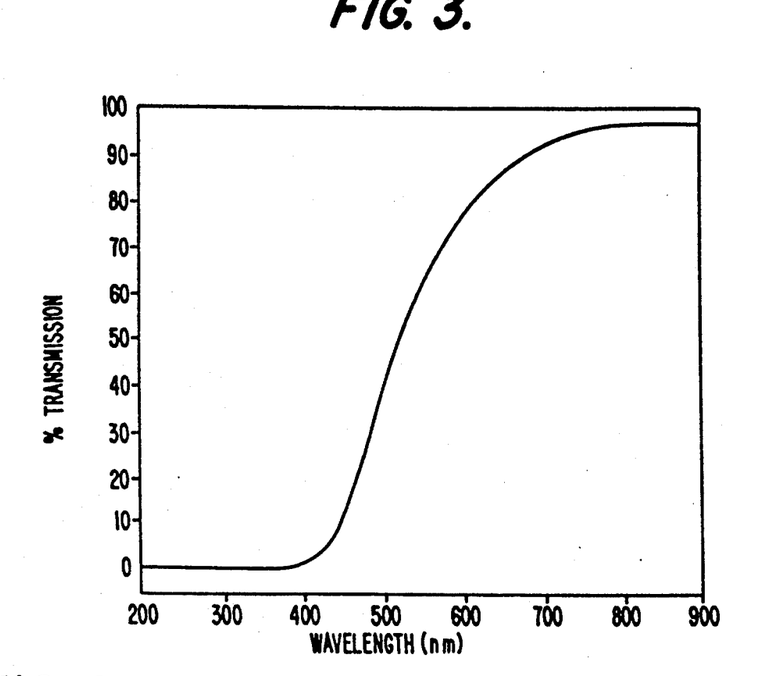

A hydrogel was prepared using MAPT in the following monomer-initiator composition. The transmission spectrum in the UV and visible range was recorded. The wavelength at 5% transmission was 432 nm for a 1 mm thick hydrogel sample (FIG. 3).

| HEMA | 20% | (2-hydroxyethyl methacrylate) |
|---|---|---|
| NVP | 60% | (N-vinylpyrrolidone) |
| MMA | 20% | (methylmethacryate) |
| MAATPT | 2% | (10-methacryloylazaphenothiazine) |
| AIBN | 0.1% | (azobisisobutyronitrile) |
| EGDM | 1% | (ethylene glycol dimethacrylate) |

EXAMPLE 7

Figure 7:
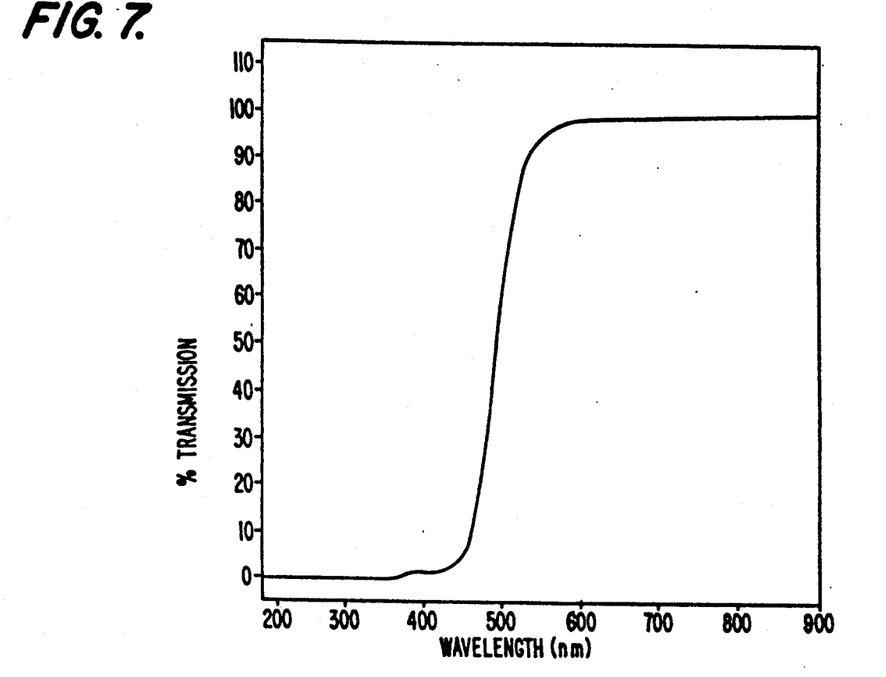

A UV absorbing hydrogel was prepared MHAPT in the following monomer-initiator composition. The transmission spectrum in the UV and visible range was recorded. The wavelength at 5% transmission was 446 nm for a 1 mm thick sample containing only about 0.5% MHACP. (FIG. 7).

| HEMA | 20% | |
|---|---|---|
| NVP | 60% | |
| MMA | 20% | |
| MHAPT | 0.5% | γ-10-(2-acetylphenothiazinyl-β-hydroxypropyl methacrylate) |
| AIBN | 0.2% | |
| EGDM | 1% | |

EXAMPLE 8

Figure 8:
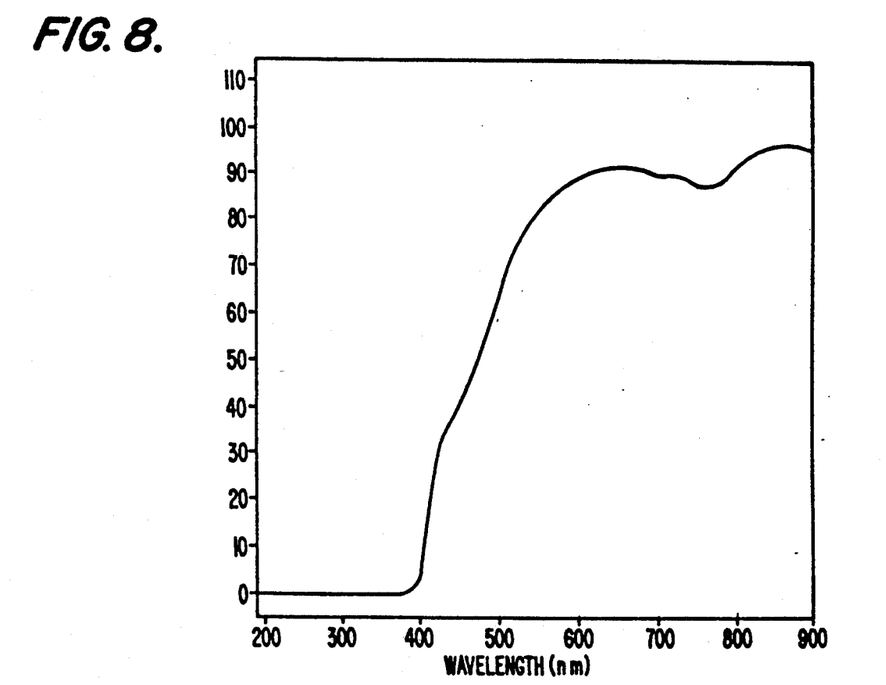

A UV absorbing hydrogel was prepared with the following monomer-initiator composition. The wavelength at 5% transmission was 400 nm for a 1 mm thick sample containing 2% AATPT (FIG. 8).

| HEMA | 20% | |
|---|---|---|
| NVP | 60% | |
| MMA | 20% | |
| AATPT | 2% | (10-acryloylazaphenopthiazine) |
| AIBN | 0.2% | |
| EGDM | 1% | |

EXAMPLE 9

Figure 9:
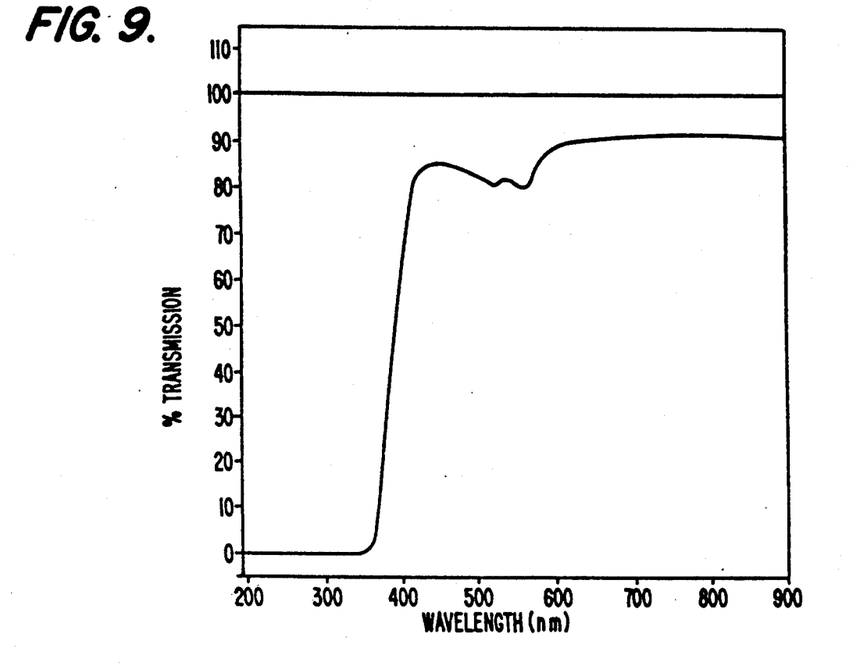

A transparent UV absorbing PMMA copolymer was prepared using MMA with 0.3 wt % MHACPT γ-[10-(2-chlorophenothiazinyl)]-β-hydroxypropylmethacrylate) and AIBN initiator. A 1 mm thick sample exhibited a UV cut-off with a 5% transmission at 365 nm (FIG. 9).

EXAMPLE 10

Figure 10:
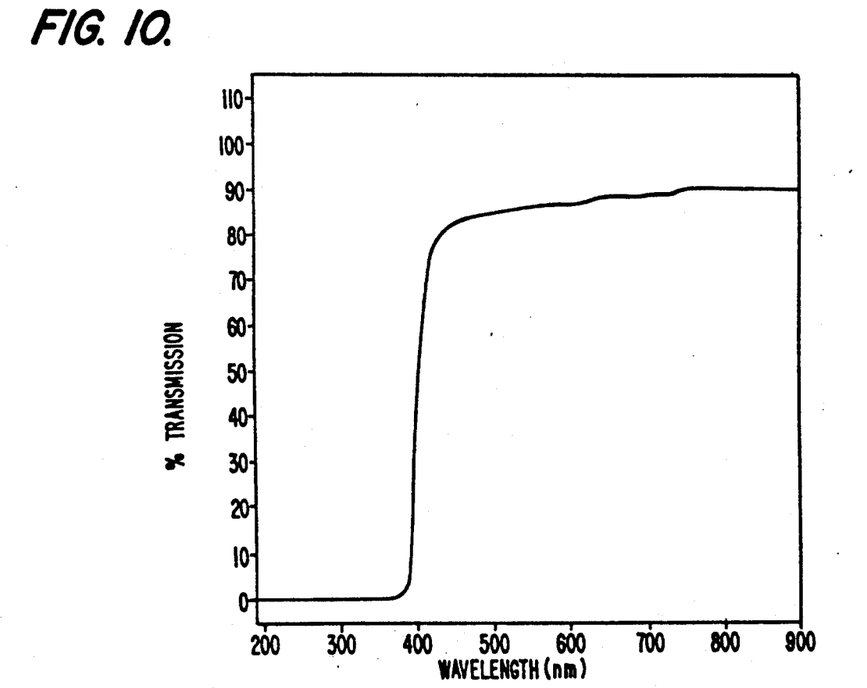

Using a 2% GMAAPT γ-10H-(azaphenothiazinyl)-β-hydroxypropyl methacrylate), a transparent PMMA copolymer (1.0 mm thick) was prepared by polymerization cast molding. The 5% transmission wavelength was 390 nm (FIG. 10).

EXAMPLE 11

An additional embodiment of this invention is the use of the new UV absorbing monomers of the invention to form linear soluble acrylic or hydrophilic copolymers with higher concentrations of the UV comonomers (e.g., 5-20 wt % UV monomer such as MHACP) to form polymeric and very strongly UV absorbing copolymers. The strongly UV absorbing copolymers may then be used as compatible polymeric UV absorbing additives with acrylic plastics or hydrogels and although not covalently bound yield stable, nonleachable, nonmigrating additives for UV absorbing acrylic or hydrogel materials.

This example describes the synthesis and characterization of a UV absorbing copolymer (MMA-MATP) of methyl methacrylate (MMA) and 10-methacryloylazaphenothiazine (MAATPT) (Formula II) and its use as an efficient compatible polymeric UV absorber in PMMA compositions useful for ocular implants.

Figure 1:
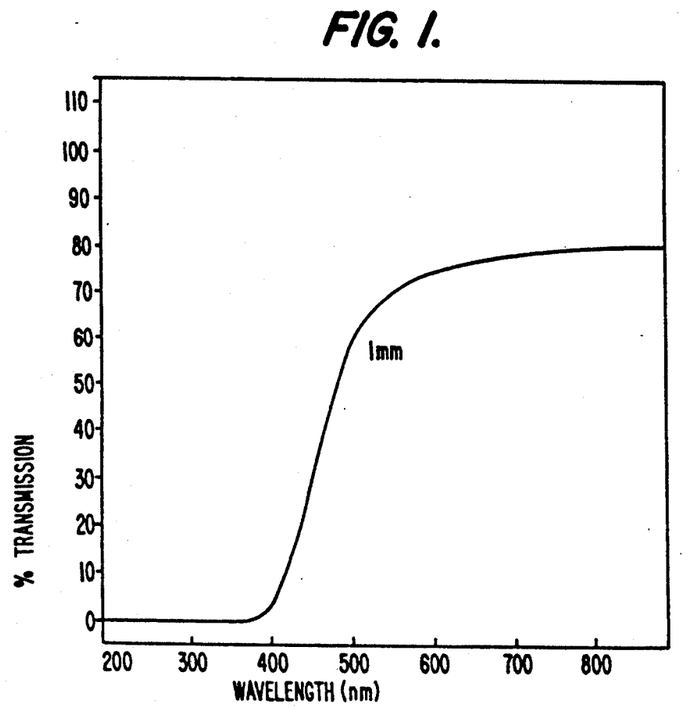
FIGS. 1-3 and 7-10 are graphical depictions of the results of the experiments described in the Examples below.

A solution of MAATPT (0.09 g), MMA (0.9 g) and AIBN (azobisisobutyronitrile) (0.003 g) in 4 ml of chloroform was placed in a glass tube. The tube was degassed by three freeze-thaw cycles (liquid nitrogen) before sealing. The polymerization was carried out at 60° C. for 50 hours. The viscous solution thus obtained was poured into a large quantity of n-hexane and the resulting precipitate was dried. After one additional reprecipitation, the copolymer (0.186 g) and AIBN (0.005 g) were dissolved in (2.364 g) MMA. This solution was used to polymerize and cast a transparent PMMA slab containing approximately 0.67% MAATPT. The wavelength at 5% transmission for a 1 mm thick slab was 404 nm as shown in FIG. 1.

EXAMPLE 12

Figure 4:
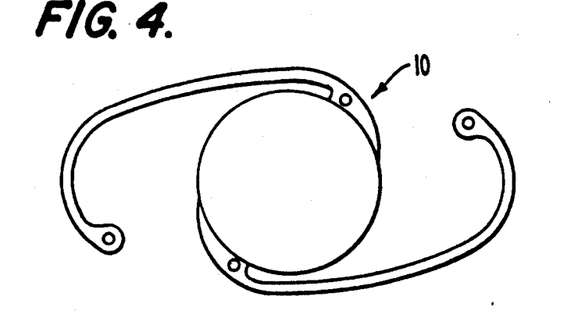
FIG. 4 depicts a top view of a one-piece intraocular lens 10.
Figure 5:
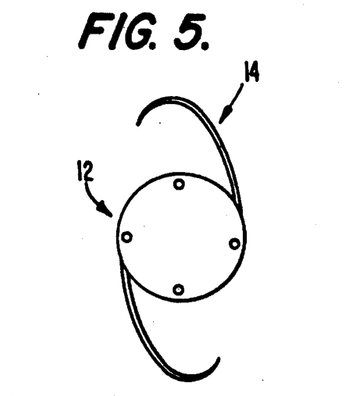
FIG. 5 depicts a top view of an intraocular lens 12 with fiber haptics 14 which may be made of a different substrate polymer than the optic.

One-piece intraocular lenses, IOLs (i.e., FIG. 4), are readily fabricated by lathe cutting cast blanks of UV absorbing PMMA prepared by the method of Examples 1, 5, 9, 10 and 11. These UV absorbing IOLs exhibit good biocompatibility when tested as implants in the posterior chamber of rabbits following extracapsular natural lens extraction. Similarly, good biocompatibility is observed for anterior chamber implants and for two-piece IOLs (i.e., FIG. 5) fabricated by molding or by lathe cutting the optic from cast blanks of the PMMA copolymers of Examples 1, 5 and 6 and fitted with polypropylene haptics.

EXAMPLE 13

UV absorbing hydrogen IOLs are fabricated by cutting and polishing cast rods of the compositions of Examples 6-8, or by casting individual lenses. They exhibit satisfactory biocompatibility as anterior or posterior chamber implants in rabbits. Flexible compositions may be inserted with folding through small incisions.

EXAMPLE 14

Figure 6:
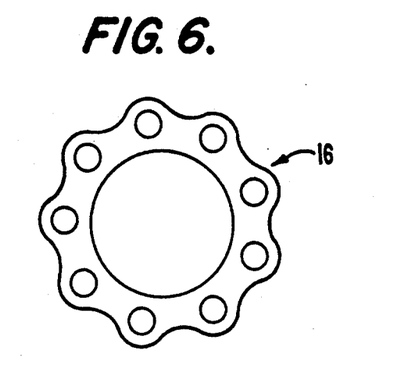
FIG. 6 depicts a top view of a keratoprosthesis 16.

Keratoprosthesis (i.e., FIG. 6) are fabricated by molding or by cutting and polishing case rolls or sheets of the UV absorbing acrylic and hydrogen compositions of Examples 1 and 5-11.

We claim:

1. An ultraviolet light absorbing polymer which comprises a homopolymer of a polymerizable monomer having the structure:

wherein:
Z is N or —CH—,
R is H or $CH_3$,
$R_1$ and $R_2$ may be the same or different and are H, alkyl or alkyloxy having from 1 to 20 carbon atoms, alkylcarboxy having from 2 to 20 carbon atoms, arylcarboxy having from 7 to 25 carbon atoms or hydroxyl;

$R_3$ is H, hydroxyl, hydroxyalkyl having from 1 to 20 carbon atoms or siloxy;

$R_4$, $R_5$, $R_6$ and $R_7$ may be the same or different and are H or halogen;

x is an integer from 1 to 20; or a copolymer thereof with an ethylenically unsaturated comonomer, said copolymer comprising an ultraviolet light absorbing effective amount of said ultraviolet light absorbing polymerizable monomer.

2. A homopolymer or copolymer according to claim 1 wherein the ultraviolet light absorbing monomer has the structure:

3. A homopolymer or copolymer according to claim 1 wherein the ultraviolet light absorbing monomer has the structure:

4. A homopolymer or copolymer according to claim 1 wherein the ultraviolet light absorbing monomer has the structure:

5. A homopolymer or copolymer according to claim 1 wherein the ultraviolet light absorbing monomer has the structure:

6. A homopolymer or copolymer according to claim 1 wherein the ultraviolet light absorbing monomer has the structure:

7. A homopolymer or copolymer according to claim 1 wherein the ultraviolet light absorbing monomer has the structure:

8. A homopolymer or copolymer according to claim 1 wherein the ultraviolet light absorbing monomer has the structure:

9. A UV absorbing copolymer according to claim 1 wherein said ethylenically unsaturated comonomer is one suitable for use in making polymers suitable for use in making optical devices.

10. A UV absorbing copolymer according to claim 9 wherein said ethylenically unsaturated comonomer is selected from the group consisting of methylacrylate, methylmethacrylates, N-vinylpyrrolidones, hydroxyethylmethacrylates, hydroxyethylacrylates, hydroxypropylacrylates, acrylamides, bisacrylamides, bisacrylates, ethylene glycol dimethacrylates, bisallylcarbonates and mixtures thereof.

11. A copolymer according to claim 9 wherein said ethylenically unsaturated comonomer is an alkylmethacrylate.

12. A copolymer according to claim 11 wherein said ethylenically unsaturated comonomer is methylmethacrylate.

13. A lens or optical device constructed at least in part from a copolymer of claim 1.

14. An ocular implant constructed at least in part from a copolymer of claim 1.

15. An intraocular lens constructed at least in part from a copolymer of claim 1.

16. A contact lens constructed at least in part from a copolymer of claim 1.

17. A keratoprosthesis constructed at least in part from a copolymer of claim 1.

18. A plastic film or molded or extruded plastic part constructed at least in part from a copolymer of claim 1.

19. A hydrogel having incorporated therein a homopolymer or copolymer of claim 1.

20. A polymer or copolymer having incorporated therein a polymer or copolymer of claim 1.

* * * * *